(12) United States Patent
Haque et al.

(10) Patent No.: US 10,857,008 B2
(45) Date of Patent: Dec. 8, 2020

(54) ADAPTER FOR SELF-ALIGNMENT IN 3 DIMENSIONAL PLANES FOR PASSIVE PROSTHETICS

(71) Applicant: Impulse Technology LLC, State College, PA (US)

(72) Inventors: Md Amanul Haque, State College, PA (US); Vamsidhar Reddy Rajula, State College, PA (US); Mst (Kamrun) Kamrunnahar, State College, PA (US)

(73) Assignee: Impulse Technology LLC, State College, PA (US)

( * ) Notice: Subject to any disclaimer, the term of this patent is extended or adjusted under 35 U.S.C. 154(b) by 0 days.

(21) Appl. No.: 16/536,935

(22) Filed: Aug. 9, 2019

(65) Prior Publication Data

US 2020/0281747 A1    Sep. 10, 2020

Related U.S. Application Data

(60) Provisional application No. 62/814,533, filed on Mar. 6, 2019.

(51) Int. Cl.
*A61F 2/66* (2006.01)
*A61F 2/76* (2006.01)
*A61F 2/50* (2006.01)

(52) U.S. Cl.
CPC .............. *A61F 2/6607* (2013.01); *A61F 2/76* (2013.01); *A61F 2002/503* (2013.01); *A61F 2002/5078* (2013.01)

(58) Field of Classification Search
CPC .. A61F 2/50; A61F 2/60; A61F 2/6607; A61F 2/76; A61F 2002/5016;
(Continued)

(56) References Cited

U.S. PATENT DOCUMENTS

| 3,754,286 A | * | 8/1973 | Ryan | ......................... A61F 2/66 |
| | | | | 623/49 |
| 5,019,109 A | | 5/1991 | Voisin | |

(Continued)

FOREIGN PATENT DOCUMENTS

| DE | 372426 C | * | 3/1923 | ............ A61F 2/6607 |
| FR | 504342 A | * | 6/1920 | ............ A61F 2/6607 |

(Continued)

OTHER PUBLICATIONS

Translation of FR504342 (Year: 1918).*

(Continued)

*Primary Examiner* — Christie L Bahena
(74) *Attorney, Agent, or Firm* — Buchanan Ingersoll & Rooney PC

(57) ABSTRACT

A self-adjusting adapter for a prosthetic leg having a foot and a leg socket has a low stiffness spring having a central opening, a high stiffness spring that has a central opening and is adjacent the low stiffness spring, a shaft or a bolt passing through the central opening in the low stiffness spring and the central opening in the high stiffness spring and a spring stiffener configured and positioned to restrain movement of the high stiffness spring relative to the low stiffness spring in a direction parallel to the low-stiffness spring. A connector for attaching the adapter to a leg socket is connected to the bolt or shaft and is capable of pivoting about an axis through the bolt or shaft. The adapter can be used an add-on component for existing prosthetic legs, or it can be integrated with foot design for the ankle-foot product category.

11 Claims, 17 Drawing Sheets

(58) Field of Classification Search
CPC ...... A61F 2002/5041; A61F 2002/5073; A61F
2002/5075; A61F 2002/5076; A61F
2002/5078; A61F 2002/5079; A61F
2002/5096; A61F 2002/5072
See application file for complete search history.

(56) References Cited

U.S. PATENT DOCUMENTS

| | | | |
|---|---|---|---|
| 5,746,773 A | 5/1998 | Littig | |
| 5,800,568 A | 9/1998 | Atkinson et al. | |
| 6,280,479 B1 | 8/2001 | Philips | |
| 6,443,993 B1 | 9/2002 | Koniuk | |
| 6,458,163 B1 | 10/2002 | Slemker et al. | |
| 7,347,877 B2 | 3/2008 | Clausen et al. | |
| 7,794,506 B2 | 9/2010 | Christensen | |
| 8,480,760 B2 | 7/2013 | Hansen et al. | |
| 9,561,118 B2 | 2/2017 | Clausen et al. | |
| 2003/0163206 A1* | 8/2003 | Yasui | A61F 2/6607 623/24 |
| 2005/0267600 A1 | 12/2005 | Haberman et al. | |
| 2007/0078523 A1 | 4/2007 | Kholwadwala et al. | |
| 2008/0262635 A1 | 10/2008 | Moser et al. | |
| 2011/0015761 A1 | 1/2011 | Celebi et al. | |
| 2012/0203359 A1 | 8/2012 | Schimmels et al. | |
| 2013/0006386 A1 | 1/2013 | Hansen et al. | |
| 2014/0008730 A1 | 1/2014 | Mitard et al. | |
| 2014/0039642 A1 | 2/2014 | Nijiman et al. | |
| 2014/0330393 A1* | 11/2014 | Ward | A61F 2/6607 623/24 |
| 2016/0242937 A1* | 8/2016 | Nelson | A61F 2/66 |

FOREIGN PATENT DOCUMENTS

| | | | |
|---|---|---|---|
| GB | 136512 A | * 12/1919 | ........... A61F 2/6607 |
| WO | 2005041814 A2 | 5/2005 | |
| WO | 2014004709 A1 | 1/2014 | |

OTHER PUBLICATIONS

Product: EliteVT; URL: https://www.endolite.com/products/elitevt.
International Search Report for PCT/US2019/065438 dated Mar. 17, 2020.
Written Opinion of the International Searching Authority for PCT/US2019/065438 dated Mar. 17, 2020.

* cited by examiner

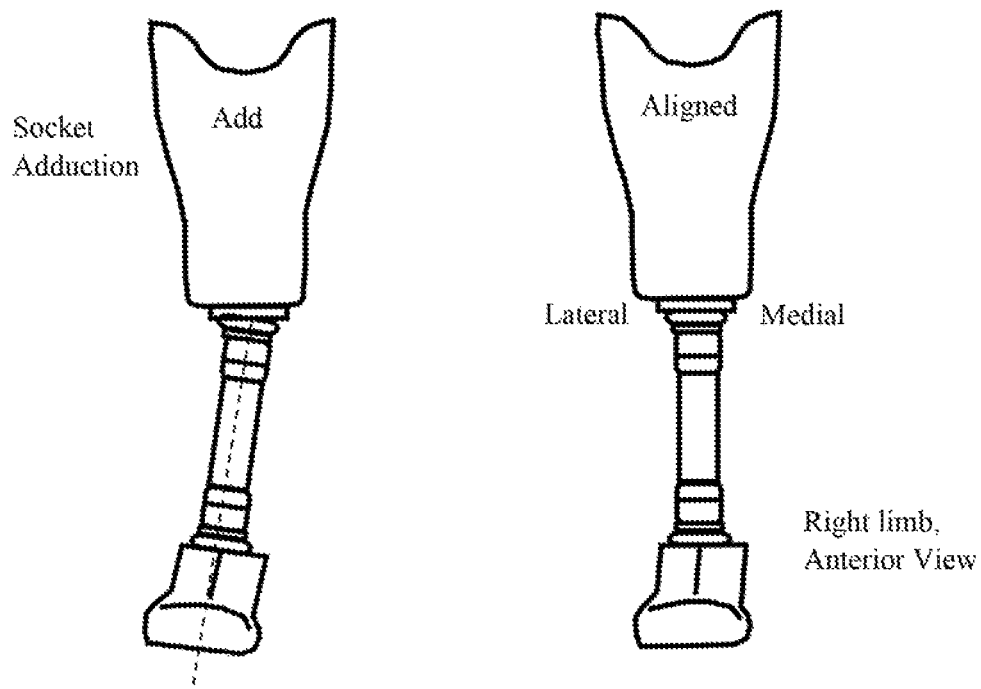
Figure 1a (Prior art)
Figure 1b (Prior art)
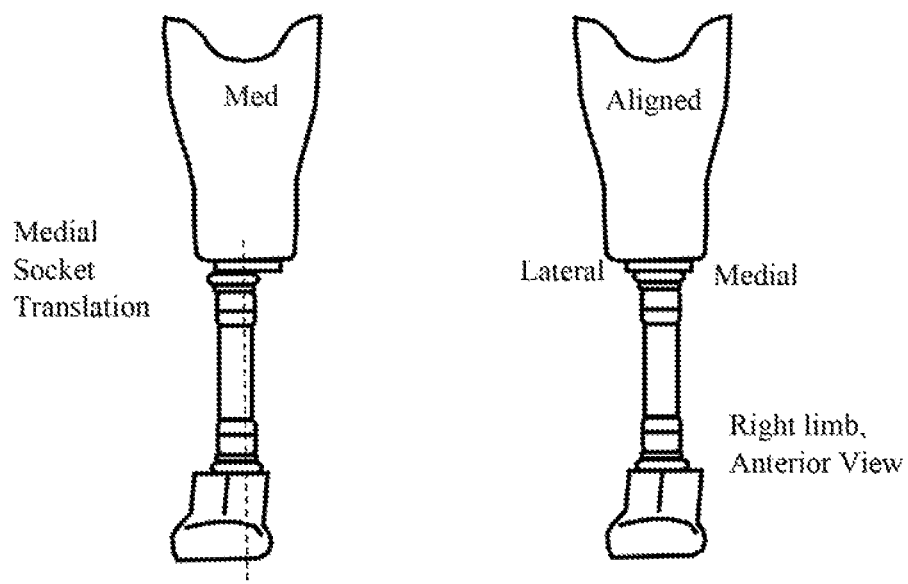
Figure 1c (Prior art)
Figure 1d (prior art)

End of heel-rocker; Moment: -5 N-m, Angle: -5°

Ground reaction force

ADAPTER FOR SELF-ALIGNMENT IN 3 DIMENSIONAL PLANES FOR PASSIVE PROSTHETICS

CROSS-REFERENCE TO RELATED APPLICATION

This application claims priority to U.S. Provisional Patent Application Ser. No. 62/814,533, filed on Mar. 6, 2019, the contents of which are incorporated herein by reference.

STATEMENT REGARDING FEDERALLY SPONSORED RESEARCH AND DEVELOPMENT

This invention was made with the United States government support under Small Business Innovative Research awards (DoD/DHA SBIR Phase I & II Contracts: W81XWH 17C 0102 & W81XWH 18C 0089). The United States government has certain rights in the invention.

FIELD OF INVENTION

The invention relates to adapters in prosthetic legs that allows certain range of motion to effectively act as a prosthetic ankle. The self-aligning adapter is an add-on component located between the foot and the pylon, thereby aligning the foot to the socket for amputee comfort. It thus also falls in the category of prosthetic ankle-foot, where the adapter is integrated with the foot.

BACKGROUND OF THE INVENTION

Prosthetic legs require careful alignment with the residual limb to avoid discomfort or pain. The alignment process is multi-step (bench, static and dynamic), 3-dimensional (sagittal, frontal and transverse planes) and iterative in nature. Both translation and rotational adjustments are made in increments to gradually reach a comfort zone for the patient. It is time consuming and subjective because of the variability in human gait as well as the adaptability to misalignment. More than 50% of amputees experience pain while walking. In the short term, they compensate any misalignment in the prosthetic leg by changing gait. However, this is not sustainable and in the longer term, problems range from tendonitis and lower back pain to amputation of the second leg or higher mortality rate in the case of diabetes. Alignment adapters and ankle-foot products are available in the market and disclosed in the literature, but they require a prosthetist to be setup. They have single or linear trend stiffness and often require hydraulic or powered mechanisms.

Prosthetic legs, whether transtibial (below knee) or transfemoral (above knee), have essential components such as socket, pylon and foot. Amputees feel pressure in the residual limb from the socket, which is the housing for the residual limb. The socket experiences force and force-couples (also known as moment of twist, or moment, in short) when the foot-pylon-socket components are misaligned. FIG. 1a shows an example of angular misalignment in a conventional prosthetic leg, compared to the aligned leg in FIG. 1b. FIG. 1c shows an example of linear misalignment in the same conventional prosthetic leg, compared to the aligned leg in FIG. 1d. Actual misalignments may have both angular and linear components. FIG. 1 is adapted from the journal article by T. Kobayashi, A. K. Arabian, M. S. Orendurff, T. G. Rosenbaum-Chou, and D. A. Boone, "Effect of alignment changes on socket reaction moments while walking in transtibial prostheses with energy storage and return feet", Clinical Biomechanics 29(1) (2014) 47-56.]

Prosthetic leg alignment is a multi-step process. A trained prosthetist performs static alignment through linear and angular corrections so that the amputee can stand with the best balance and comfort. Next, dynamic alignment is performed with 3-dimensional corrections (sagittal, frontal and transverse planes) as the amputee walks and communicates with the prosthetist regarding the balance and comfort. Since the socket axis and ground reaction force (GRF) direction can have a large range of variation during the gait cycle, dynamic alignment is challenging, even with robotic or microprocessor-controlled prostheses.

The market and literature contain alignment adapters that can translate, tilt or rotate the prosthetic components. While these aligners possess adequate degrees of freedom in motion, they do not self-align. Or in other words, they require manual intervention from the prosthetist if there is any deviation from the original adjustment. This is a major problem because the prosthetist never makes all the required adjustments at the same time. Rather, these are achieved through many time-consuming iterations from the prosthetist and the amputee. Therefore, existing alignment products do not reduce the complexity of the number of variables and their interdependence. The human to human variance does not allow the prosthetist to develop a scheme for mitigating the dynamic alignment problem. As a result, the problems of accurate diagnosis and remediation remain intractable. Perhaps, the best evidence to draw this conclusion from a review of 35 years of research which outlines 43 variables but could not even assign a statistical confidence on most of these. E. S. Neumann, "State-of-the-Science Review of Transtibial Prosthesis Alignment Perturbation," JPO: Journal of Prosthetics and Orthotics 21(4) (2009) 175-193.

Prosthetic Alignment Adapters are add-on components to prosthetic leg that allows linear (or off-set) and rotational motion between prosthetic components such as foot and pylon for static and dynamic alignment. Published United States Patent Application No. US20050267600A1 discloses an alignment assembly for a modular prosthetic device. The device includes many modules than can be added or removed to add additional degrees of freedom, or to restrict movement. Linear movement is allowed about two orthogonal axis. Rotational and angular adjustments are made about the three orthogonal axis. Locking mechanisms are included on the dovetails slots which limit motion as desired. This device is intended both for use transtibial and/or transfemoral. Published United States Patent Application No. US20110015761A1 discloses a prosthetic device that allows for alignment of the prosthesis about the central axis. There is a hub that connects the socket and the prosthetic foot. The hub allows for two degrees of freedom, rotation about the central axis and translation along the first central axis. A clutch mechanism is in one of two positions which limits and allows movement respectively. Alignment of the device can be done while the amputee is wearing the device.

Published PCT Application No. WO2005041814A2 discloses a device that performs offset alignment between two prosthetic components by a selected distance along an alignment axis. The invention comprises first and second members. The first member has a channel and the second member has a bar for being adjustably connected to the channel along the alignment axis. A set screw can be adjusted through a hole in the wall of the channel in a direction generally perpendicular to the alignment axis to contact the bar and hold it stationary within the channel. One or both of these members can be rotatably connected to prosthetic components.

U.S. Pat. No. 6,458,163 B1 discloses a device that is placed within a prosthesis that allows for alignment of the limb. The device allows for translation and rotation. Rotation is controlled by a ring with internal threads and a ring clamp. The device is intended for both above, and below knee amputees. Translation is restricted via set screws into the dovetail section of the device.

Another type of adapter is the passive ankle or ankle foot, where the adapter is not an add-on component but is integrated to the foot. While alignment adapters behave like rigid components after the alignment is over, ankle or ankle-foot are prosthetic components that allow certain degrees of freedom during walking. Multi-axial foot and/or ankle-foot provide rotational degree of freedom that could be beneficial for amputees. In the existing products, the multi-axial motion does not come from the ankle, but from the foot design. The stiffness of such motion is generated and/or often adjusted with computer and/or hydraulic control. A key characteristic of these products is that after the prosthetist sets up their stiffness, it does not change as the amputee walks on them. This is not the optimal solution, because for real-time alignment, highly non-linear stiffness mimicking natural ankle or foot is needed. For example, the stiffness of the ankle-foot needs to be very low at the first 5-10% of the gait cycle. Else, alignment is not possible. Right after that, the stiffness must be very high to generate the propulsive moment. For example, in the sagittal plane, the stiffness must be asymmetric (<1 N-m per degree from 0° to −5° ankle angle and >5 N-m per degree from −5° to +10° ankle angle). Since all existing passive ankle foot have fixed stiffness, they are not able to provide the desired alignment effects.

U.S. Pat. No. 7,347,877 B2, discloses a foot prosthesis with resilient multi-axial ankle. This device is an ankle that is located between the pylon and the foot of the prosthesis. The ankle incorporates multiple stiffnesses in different locations of the foot. The lateral side of the foot is relatively stiffer than the medial side of the foot. This stiffness difference is accomplished by making the openings in the material of the ankle larger on the medial side. The ankle is capable of flexing in multiple directions.

Published United States Patent Application No. US20080262635A1, discloses a self-aligning prosthetic ankle-foot assembly. The ankle contains pistons which control the damping resistance. Hydraulic damping of dorsi and plantar flection are thus controlled. This device was designed to address stair and ramp walking specifically. The range of dampening is continuous throughout the step.

U.S. Pat. No. 8,480,760 B2 discloses an improved system for use in rehabilitation and/or physical therapy for the treatment of injury or disease to the lower limbs or extremities. The system can enable an amputee to proceed over any inclined or declined surface without overbalancing. The system is mechanically passive in that it does not utilize motors, force generating devices, batteries, or powered sources that may add undesirable weight or mass and that may require recharging. The system is self-adapting to adjust the torque moment depending upon the motion, the extent of inclination, and the surface topography. An additional advantage of the improvement is that the system can be light and may also be simple to manufacture.

Published United States Patent Application No. US20120203359A1 discloses a passive lower limb prosthesis that contains two degrees of freedom. A large mechanism contains many compression springs to achieve a working ankle. This device is largely passive, which means it does not use sensors or actuators of any kind. One of the degrees of freedom in this design allows the prosthesis to compress slightly under the weight of the user. The other degree of freedom allows rotation about the prosthetic ankle joint. The first degree of freedom absorbs energy and supplies it to the second, in order to aid the energy that was captured during dorsiflexion.

Published United States Patent Application No. US20130006386A1 discloses an ankle-foot prosthesis and orthosis capable of automatic adaptation to sloped walking surfaces and methods of use. An amputee can use this device to walk across an inclined or declined surface without overbalancing. This system is purely mechanical and does not utilize motors, or powered sources. This device self-adapts to the motion to adjust the torque moment it experiences. Included below is an image of the equivalent spring systems that the prosthesis is able to achieve during walking due to its design.

U.S. Pat. No. 6,443,993 B1 discloses a self-adjusting prosthetic ankle apparatus. This computer-controlled design incorporates an upper portion and lower portion that attach to a leg pylon and foot plate respectively. The device includes damping mechanisms. The sensing module of this device is able to detect when the ground is contacted and determine what stage of the walking cycle a user is in. The ankle system also automatically adjusts to different heel heights of footwear without user input. The two cylinders in the front and rear of the prosthesis allow for traversing sloped terrain.

Published United States Patent Application No. US20140088730A1 discloses an ankle-foot prosthesis which contains a foot plate, ankle frame and a yoke. There is a damping system in the heel of the device to reduce the impact during heel strike. The hydraulic damper can be switched between high and low settings. The invention is said to be able to adapt to sloped terrain and provide stability when standing and swaying. This device has only a few parts, which is said to make it easy to maintain.

Published United States Patent Application No. US20140039642A1 discloses a prosthetic ankle that is not powered and consists of purely mechanical components. The foot portion includes three members that act as springs when walking. The prosthesis is capable of translation and rotation of the foot. The ankle is also able to undergo dorsiflexion, plantarflexion, inversion and eversion. A four-bar linkage is included at the ankle to allow for these rotations.

None of the alignment adapters in the literature allows alignment motion in all three planes. Two or more such adapters may be combined to provide such complete motion, but that increases size and weight. Since they are rigid elements, none of the alignment adapters allow tunable and variable stiffness like a natural leg. They only enable the prosthetist to change the alignment between foot, pylon and socket. Similarly, they do not allow rotational compliance like an ankle.

Existing multi-axial ankle or foot-ankle products allow motion 2 planes and rarely permit motion in all three planes simultaneously. Most of them work in the sagittal plane. Sagittal plane has the highest moment, but even small misalignment in other planes are equally painful. Most of the ankle or foot-ankle products use hydraulic actuators or dampers to achieve desired stiffness. For the same reason as mentioned above, the stiffness value of the ankle cannot be changed automatically as the leg goes from plantarflexion to dorsiflexion. Rather, the hydraulics need to be tuned manually to increase or decrease the stiffness. Finally, none of the adapters or ankles or ankle-foots are designed to be assembly free or one-piece product. Or in other words, they are not amenable to 3D printing.

It is important to note that some of the above-mentioned shortcomings are addresses by a third category of prosthetics, namely the Powered or Active Ankle or ankle-foot. These are active or robotic prosthetic components that allow certain degrees of freedom utilizing sensors, actuators and electronics. The present invention, on the other hand, is passive in nature and does not fall in this category.

SUMMARY OF THE INVENTION

We provide an adapter for a prosthetic leg that overcomes many of the problems associated with misalignment by aligning itself in real-time as the user walks. Our adapter is a 6 degrees of freedom (dof) mechanism with high non-linearity in stiffness. Depending upon the ground reaction force (GRF) and the angle of the foot with respect to the ground, it passively senses the phase of the gait. It then self-aligns the prosthetic leg in all three planes through simultaneous translation and rotation. More importantly, the stiffness of the mechanism closely mimics that of the natural ankle during the heel-rocker and ankle-rocker phases of the human gait cycle. This is achieved by an innovative design combining two sets of planar compliant structures, each with 6 degrees of freedom. The first structure is more compliant (<1 N-m/° of rotation) and mimics the ankle during heel-strike by allowing rotational motion to produce the self-aligning effect. In addition, it also provides small linear motion for enhanced alignment as well as shock absorbing. The compliant structures are accommodated by other structures that make their stiffness highly non-linear. This is important for stability in walking. The second structure is stiffer (>5 N-m/° of rotation) to generate the large moment required for walking. The adapter can be embodied as an add-on component, such as an alignment adapter, that can be mounted between conventional passive foot and pylon to provide self-aligning feature. Alternatively, the adapter can be embodied as an ankle-foot unit, where the adapter is integrated with a foot component to provide ankle characteristics.

Even though our adapter is a passive mechanism, it can be applied to active (robotic or computer-controlled) prosthetics for enhanced agility and performance. A unique feature of the invention is that it can manufactured assembly-free or as one-piece through the 3D printing technique.

Any prosthetic leg fitted with the invented mechanism will require little prosthetist attention. Therefore, the advantage is drastic reduction in prosthetist care time. Over the usage, the patient will experience less pain and discomfort, exert less physical labor in walking and prevent long-term physiological damages. Since the invention is a passive mechanism, and is amenable to 3D printing, it will be significantly lower cost compared to active prosthetics.

Our adapter also has the followings attributes:
(a) The product is a passive (no sensor, actuator or electronics) alignment adapter, which can be mounted between the prosthetic foot and the pylon. Essentially, it acts as ankle joint with both linear and rotational compliance in all three planes of motion.
(b) The product can also be integrated with a foot to embody an ankle-foot.
(c) The product self-aligns the prosthetic leg and generate variable ankle stiffness mimicking a natural ankle in real time, unlike other existing products that require prosthetist intervention.
(d) The product has highly non-linear, rotational and linear (6 degrees of freedom) stiffness. It is very compliant in the <10% of the gait cycle and then very stiff afterwards. This early gait cycle compliance is key to self-alignment because the pylon can align itself relatively better before the entire body weight is applied. Such self-alignment takes place in real-time (no intervention) in all three planes of motion.
(e) The product mimics the plantarflexion and dorsiflexion stiffness in a natural leg, therefore is effective for slopes, stairs and uneven terrain.
(f) The product design is directly amenable to 3D printing as well as conventional machining. It does not involve hydraulics or other difficult to manufacture or assemble mechanism. Therefore, it does not require maintenance. It is also suitable for all weather and outdoor conditions.
(g) The product is compatible with all existing prosthetic feet, whether rigid, multi-axial or computer controlled.
(h) The product build height (vertical) is only 1 inch or less, making it a convenient fit for most patients who have a prosthetic foot.

Other objects and advantages of our invention will become apparent from a description of certain present preferred embodiments thereof shown in the drawings.

BRIEF DESCRIPTION OF THE DRAWINGS

FIGS. 1a and 1b show examples of angular misalignment in a conventional prosthetic leg.

FIGS. 1c and 1d show examples of linear misalignment in the same conventional prosthetic leg.

DESCRIPTION OF PRESENT PREFERRED EMBODIMENTS

Figure 2A:
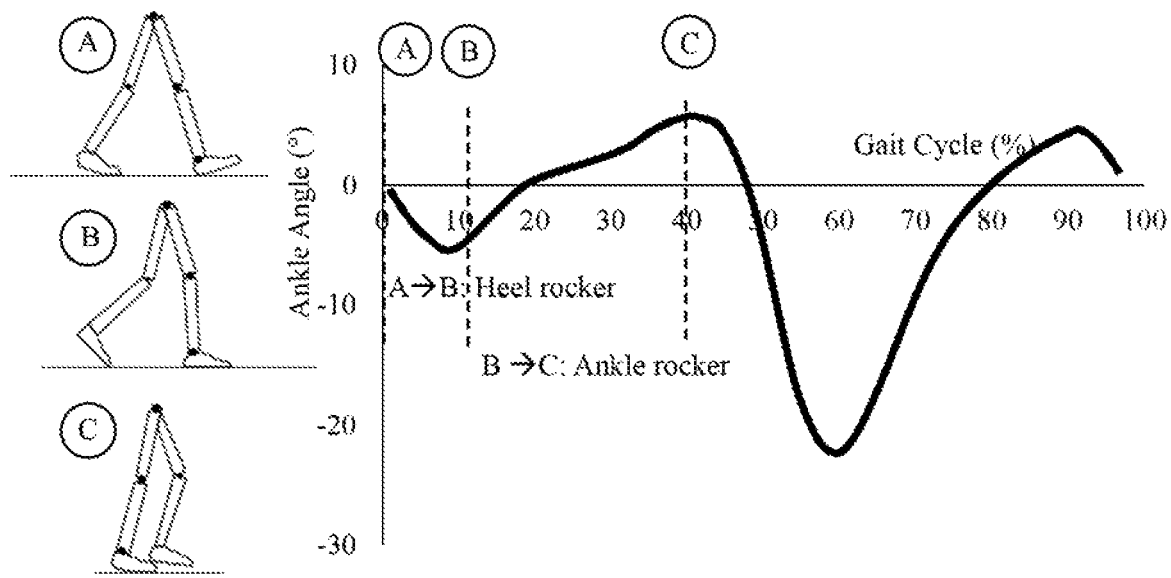
FIG. 2a is a graph of the gait cycle showing three phases (heel, ankle and fore-foot rocker) in healthy humans.

To explain the product function, we provide some background of the gait cycle in FIG. 2a. The human gait cycle starts with the heel rocker phase, where the ankle provides up to −5° of plantarflexion angle and the moment is about −5 N-m. Our adapter achieves similar rotational and linear compliance in this phase to perform the self-alignment because a natural leg does the same. Interestingly, none of the existing alignment adapters function in this phase, because they are manually setup by the prosthetist even before walking. Our product acts in real time not only during this phase, but also in the second phase.

The second phase of gait is called the ankle-rocker, where the rotational stiffness in the sagittal plane becomes abruptly high and the direction of ankle rotation reverses from plantarflexion to dorsiflexion. The rotational stiffness must increase highly non-linearly to allow the body propulsion forwards. The ankle angle versus ankle torque (moment) diagram is given in FIG. 2b. Such abrupt reversal or angle and increase of rotational stiffness is the key challenge our invention handles very efficiently.

Figure 2B:
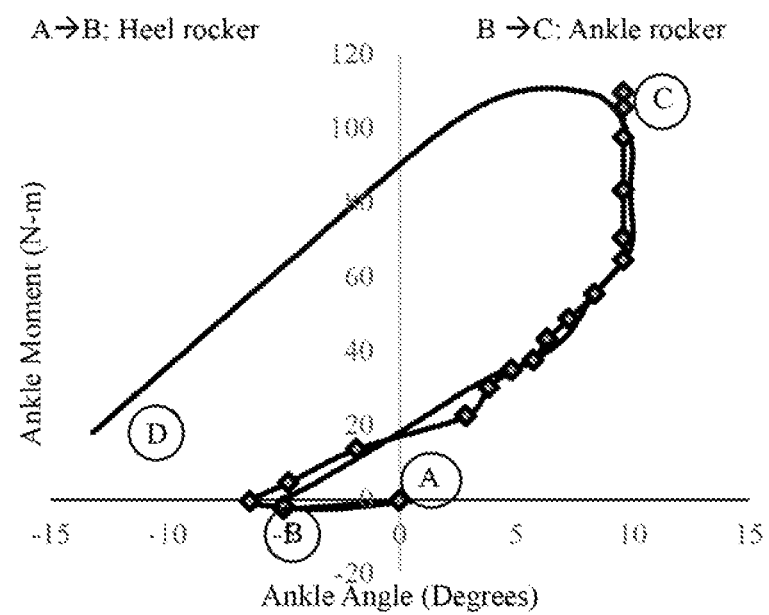
FIG. 2b is a graph in which the solid line shows ankle angle vs. ankle torque or moment in healthy humans with diamond marked data showing performance of the adapter of this invention.

FIG. 2b shows how the present product functions using the diamond shaped data markers as compared to natural ankle function shown in solid line. The present product function is shown during two phases. The first phase is between points A and B while the second phase is between points B and C. The third phase, between points C and D, is called fore-foot rocker and is not an ankle-activity. The products disclosed and claimed herein can mimic the natural ankle for the first two phases.

Figure 3:
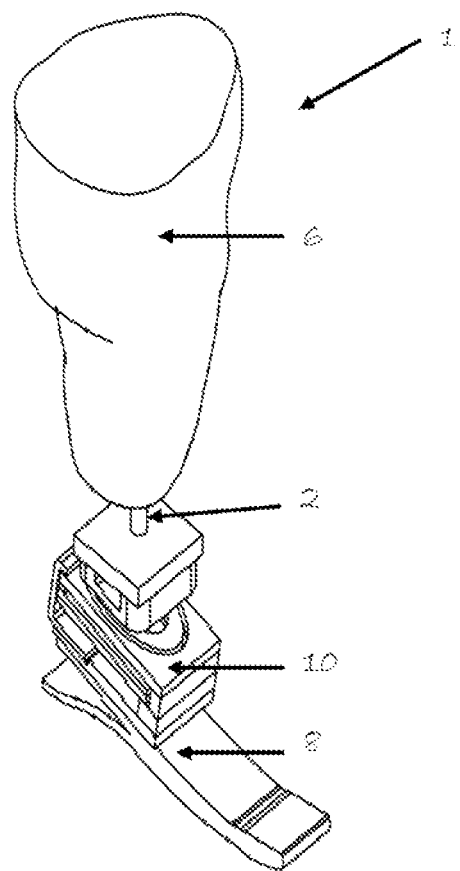
FIG. 3 shows a present preferred embodiment of our adapter (as an add-on component) connected between a prosthetic leg socket and a foot.
Figure 4:
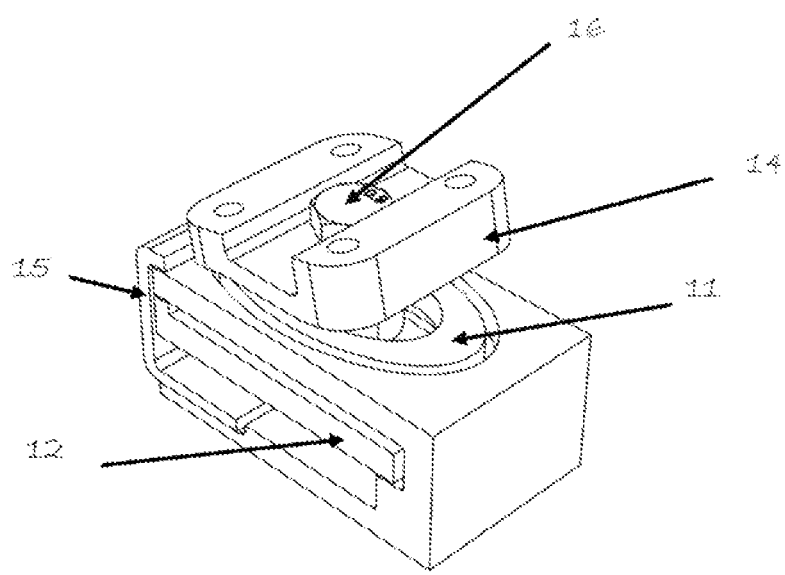
FIG. 4 is a perspective view of the embodiment of our adapter shown in FIG. 3.
Figure 5:
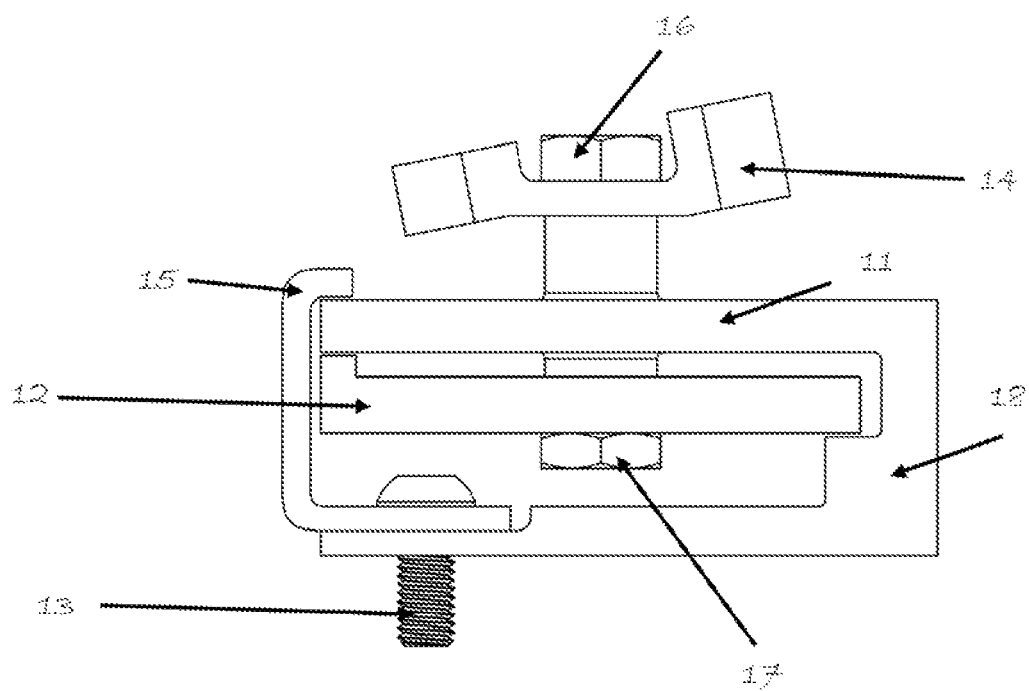
FIG. 5 is an end view thereof.
Figure 6:
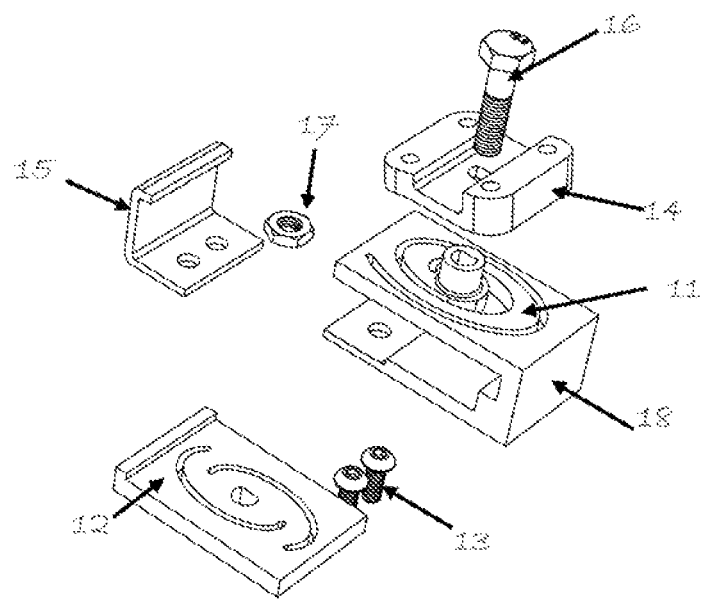
FIG. 6 is an exploded view thereof.

Referring to FIG. 3, a present preferred embodiment of our self-aligning adapter 10 is connected between a prosthetic socket 6 and a foot 8 in a prosthetic leg 1. The embodiment shown in FIGS. 3 through 6 is an add-on component (a self-aligning adapter) that is mounted on a foot 8 and connected to a pylon 2 or socket 6. In FIG. 4, we show a low stiffness spring 11 which is essentially a 6 dof planar compliant spring shown in FIG. 7 or FIG. 8. FIG. 5 shows how the low stiffness spring 11 is cut out of the structural frame 18. This frame 18 also accommodates a high stiffness spring 12 inside its cavity. Like spring 11, spring 12 is also a 6 dof planar compliant spring, except is stiffer. A spring stiffener 15 is attached to the structural frame 18, which acts as mechanical stop to the spring 11 as well as spring 12, thereby effectively non-linearly stiffening them. A top adapter connector 14 is connected to the structural frame 18 by screw 13 by bolt 16 and nut 17. An unthreaded shaft may be used in place of the bolt. The leg socket 6 or pylon 2 is connected to the top adapter connector 14. FIG. 6 shows the physical connections of the components using an exploded view. The self-aligning adapter can be connected to prosthetic legs with existing socket and foot components.

Figure 7:
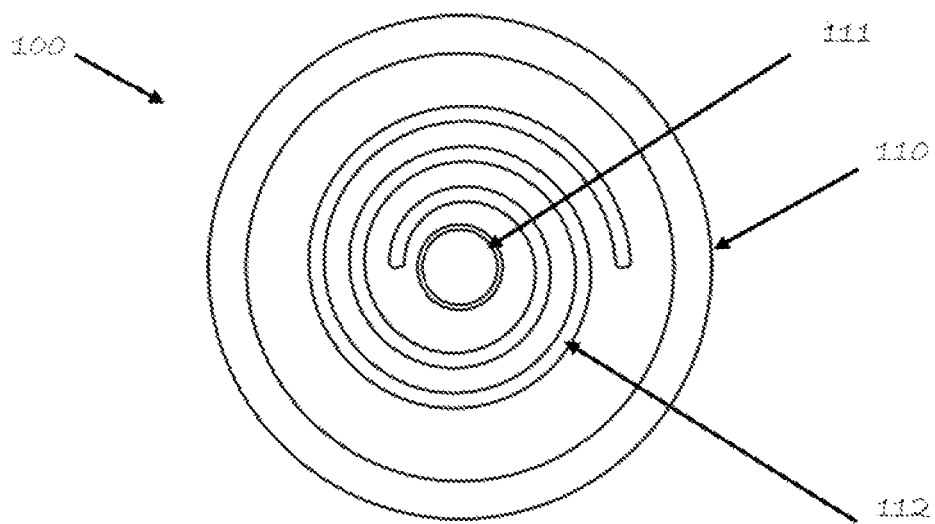
FIG. 7 is a top plan view of a present preferred embodiment of a 6 degree of freedom planar compliant structure (before loading).

Our product exploits the planar (spiral, elliptical or other possible shapes) compliant structures shown in FIGS. 6 and 7, each as 6 degrees of freedom springs. It employs two such springs physically connected by a core rod and a housing in a unique way to act as non-linear stiffener for the springs. The physical connection of the two springs are uniquely designed so that during the heel-rocker phase, only the low stiffness spring engages. At the end of this phase, the amputee has the foot flat on the ground and the second phase (ankle-rocker) begins. In the second phase, the two springs become parallel connected, making high stiffness spring the dominant one. The resulting moment vs ankle angle values are shown in FIG. 2b using diamond shaped data markers. The overall result demonstrates the biomimicry of a natural ankle by the invention in the sagittal plane.

Figure 8:
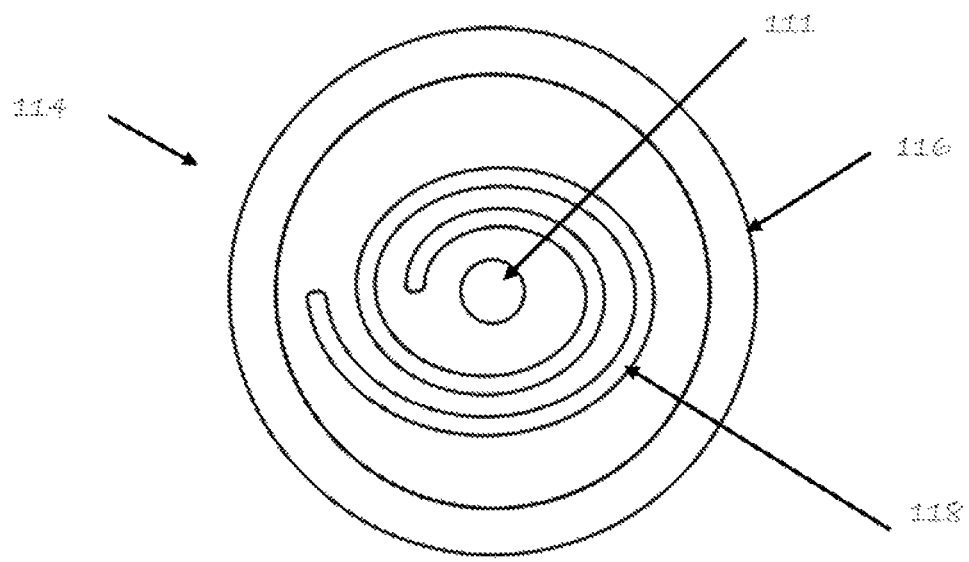
FIG. 8 is a top plan view of another present preferred embodiment of a 6 degree of planar compliant structure (before loading).
Figure 9:
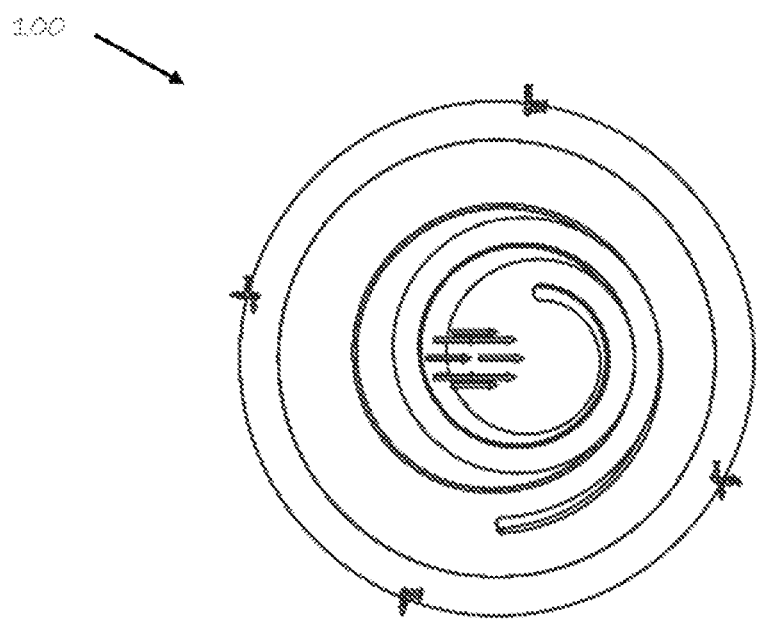
FIG. 9 is a top plan view of a present preferred embodiment of a 6 degree of freedom planar compliant structure that demonstrates linear motion of the planar compliant structure.
Figure 10:
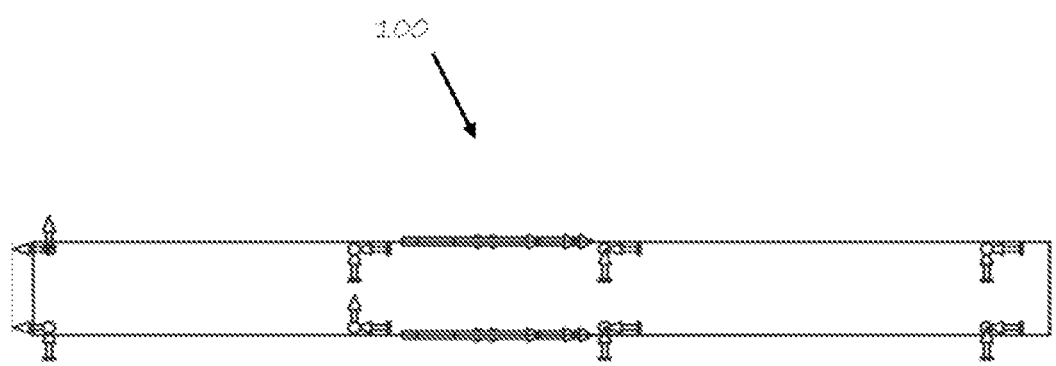
FIG. 10 is a side view of the embodiment shown in FIG. 9.
Figure 11:
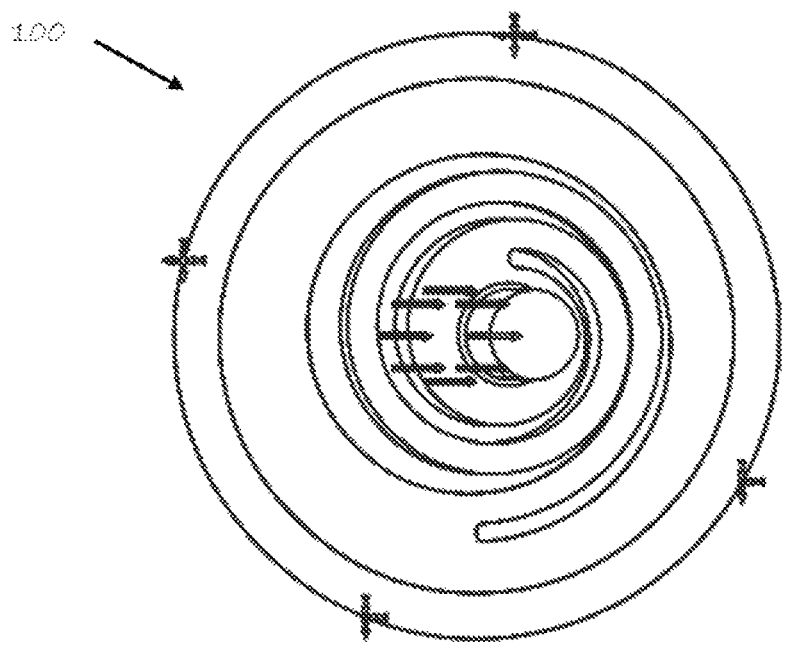
FIG. 11 is a top plan view of a present preferred embodiment of a 6 degree of freedom planar compliant structure that demonstrates rotational motion of the planar compliant structure.
Figure 12:
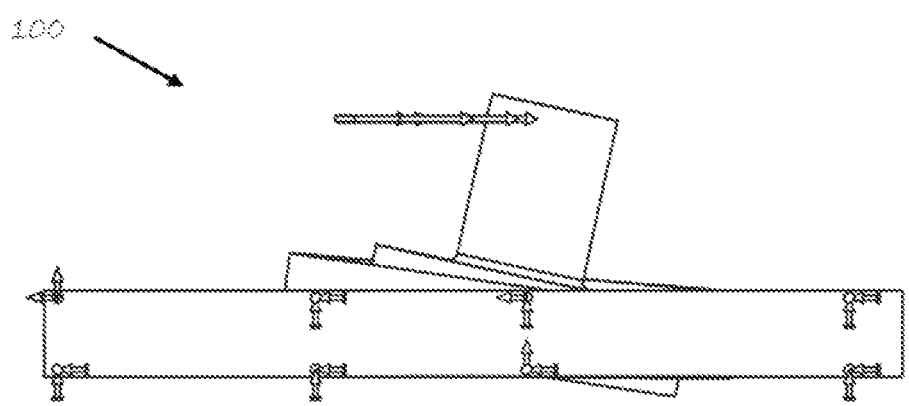
FIG. 12 is a side view of the embodiment shown in FIG. 9.

A unique component of the present invention is the planar compliant structure that passively senses the various values of applied moment (negative for heel-rocker phase and positive for ankle-rocker phase). Or in other words, it can sense the various phases of walking and can soften or stiffen itself to produce self-aligning features in heel-rocker and propulsion ankle-rocker. This happens in real time in all three planes of motion and not just the sagittal plane. This is obtained naturally by the compliant structures because they have 6 degrees of freedom (3 linear and 3 rotational). This arises naturally because the geometric symmetry of the structure. FIGS. 7 and 8 show two possible embodiments of these planar structures. The first embodiment 100 (in FIG. 7) has a cylindrical disc shaped body 110 with center opening 111 through which the mounting bolt may pass and a circular spiral opening 112 around the center opening. The spiral can be circular or elliptical depending of the desired stiffness and the available space. The second embodiment 114 (in FIG. 8) has cylindrical body 116 with center opening 111 through which the mounting bolt may pass and an elliptical spiral opening 118 around the center opening. FIGS. 9 and 10 show the change in shape of the first embodiment 100 during linear motion, while FIGS. 11 and 12 show the change in shape of the first embodiment 100 during rotational motion. In a typical assembly, the body 110 or 116 is held rigidly while the load is applied through the core (111). The location around the core is essentially a 6 dof spring because it can experience linear and rotational motion in three axes. The stiffness of these springs is determined by the geometry of the spiral (112 or 118) and thickness of the disc shaped bodies 100 or 114.

It is important to note that these planar compliant structures have nonlinear stiffness. As shown in FIGS. 9 and 11, the various facets of the structures make contact with each other upon deformation. These contact points are shown with arrows. Upon this contact, the structures stiffen up. Such change is stiffness is non-linear. Another way the stiffness can be non-linear is if the structures are nested with rigid structures (stiffeners). Here, upon initial deformation, the structures are blocked by the stiffeners and the resultant is non-linear stiffness increase.

In addition to the 6 degrees of freedom of motion, the non-linear stiffness changing capability is of tremendous significance for the present invention. Human gait phases require time and position dependent nonlinear changes in stiffness. For example, the end of the heel rocker and ankle rocker phases require significant stiffening of the low and high stiffness springs.

Figure 13:
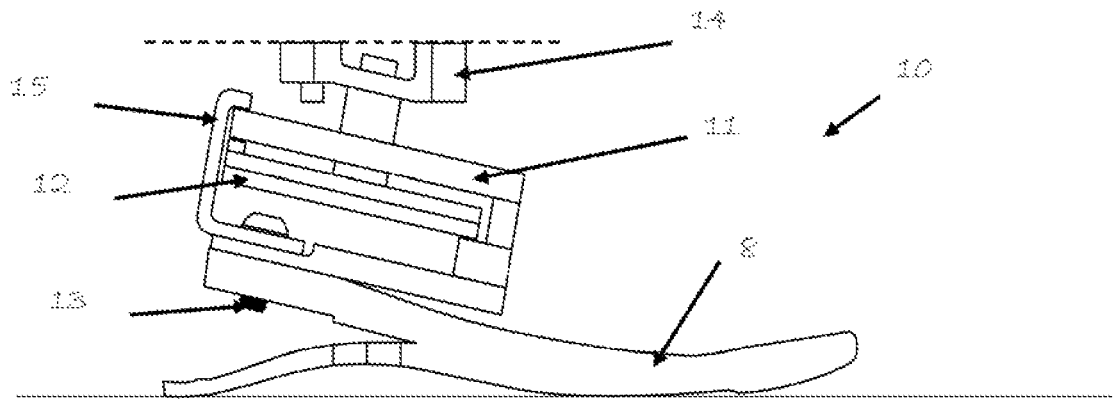
FIG. 13 is a side view of the embodiment of our self-aligning adapter shown in FIGS. 2 through 6 after it is attached to a foot and is in no-load condition.
Figure 14:
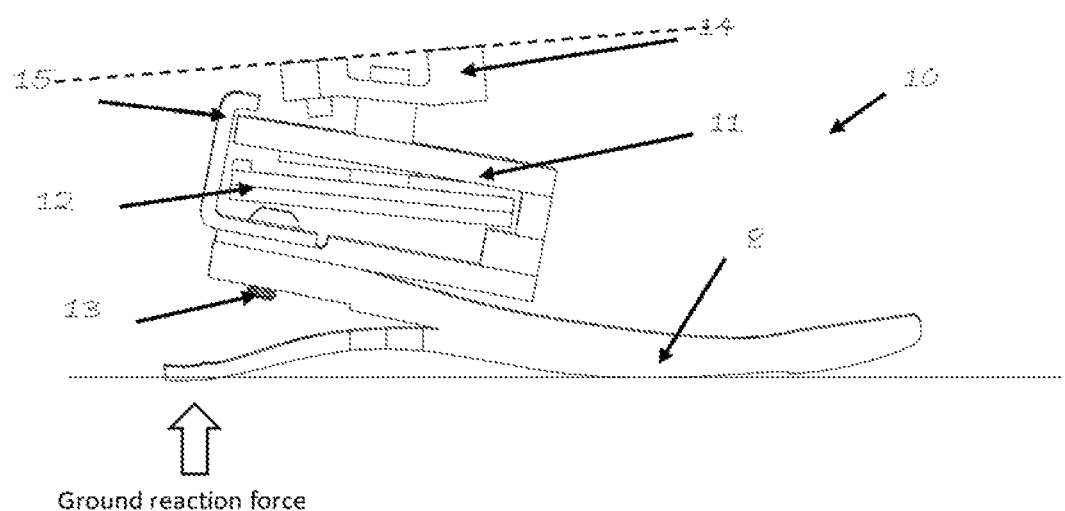
FIG. 14 is a side view of the embodiment shown in FIG. 13 at the end of the heel-rocker phase (planter-flexion).

Finite element analysis (FEA) was performed on a detailed product model of the embodiment shown in FIG. 4. The numerical results are shown in FIG. 2*b*. As previously described, that figure provides a visualization from the finite element simulation for the two different phases of the gait cycle. In the first phase, from A to B in FIG. 2*b*, the ankle moves from 0° to −5° with very low ankle rotational stiffness. This is shown schematically in FIGS. 13 and 14. The torque value at the end of this phase shown in FIG. 14 is only 2-5 N-m as the ground reaction force reached the maximum value. For able bodied persons it is about 120% of the body weight. For amputees, it could be as low as 80%. This suggests that low stiffness is the key to alignment of the foot before the entire body weight is applied. FIG. 13 shows our adapter 10 attached to a foot 8 in its neutral or no-load condition. FIG. 14 shows the adapter 10 at the end of heel-rocker phase (point B in FIG. 2*b*). Finite element results show only low stiffness spring being activated. Finite element simulation also shows that depending on the misalignment and the applied load, the self-aligning adapter can translate in the x-y plane as well as the vertical (z) plane. Such translation in the 3D space minimizes linear misalignment in the prosthetic leg. In addition, the low torque spring can also perform rotation along all 3 axes to minimize rotational misalignment.

Figure 15:
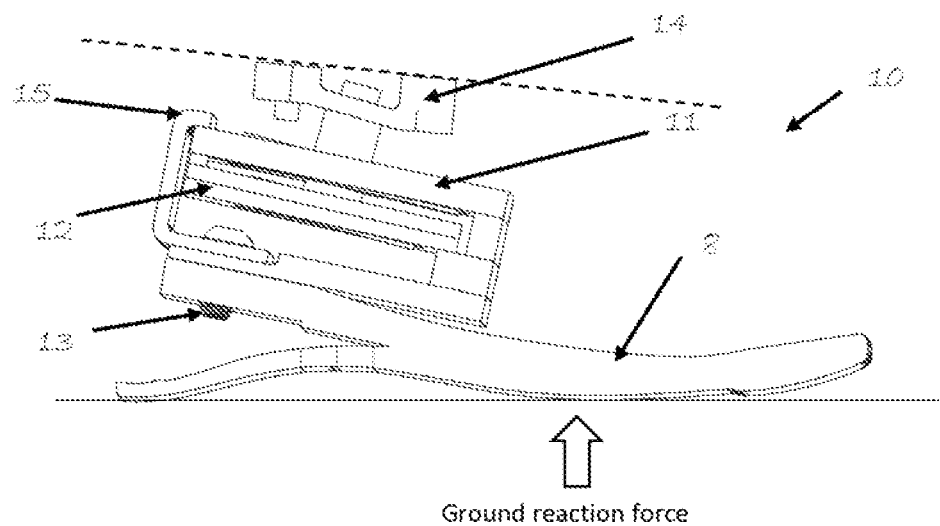
FIG. 15 is a side view of the embodiment shown in FIG. 13 at the end of the heel-rocker phase (dorsi-flexion).

In the second phase, between points B and C in FIG. 2*b*, the foot 8 remains flat on the ground as the ankle rotates from −5° to +10° (plantar to dorsiflexion) with very high rotational stiffness. FIG. 15 shows the self-aligned adapter 10 at the ankle-rocker phase (dorsi-flexion). As the adapter starts rotating from plantar to dorsi flexion, there is an abrupt and large change in stiffness, shown in FIG. 2*b*. This is achieved by the self-aligning adapter, where the unique assembly of the two springs and the rigid constraint (identified in FIG. 4 as spring stiffener 15) shift the load towards the high torque spring 12. At the end of this phase, the motion of this spring becomes completely blocked by the rigid constraints at both ends, which helps the adapter 10 to achieve the very high torque (>100 N-m) without excessive ankle rotation. It is important to note that existing passive prosthetic legs use roll over of the foot on the ground and this takes place without any real rotation in the ankle area. In comparison, the present invention is passive, but it acts like a natural human ankle.

Figure 16A:
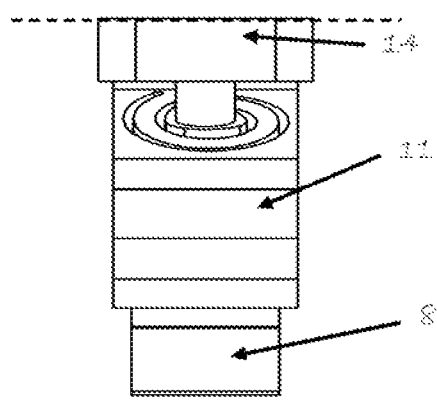
FIGS. 16a and 16b are front views of the embodiment shown in FIGS. 13 through 15 showing how our self-aligning adapter provides rotational alignment in the coronal plane.
Figure 16B:
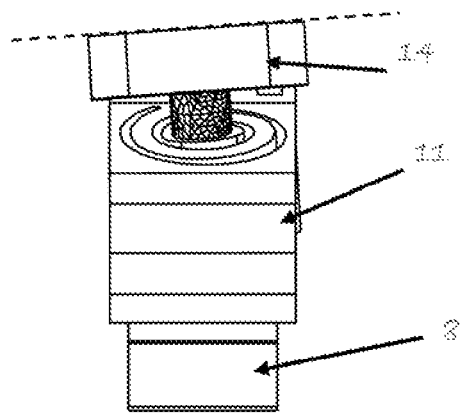
Figures 16C, 16D:
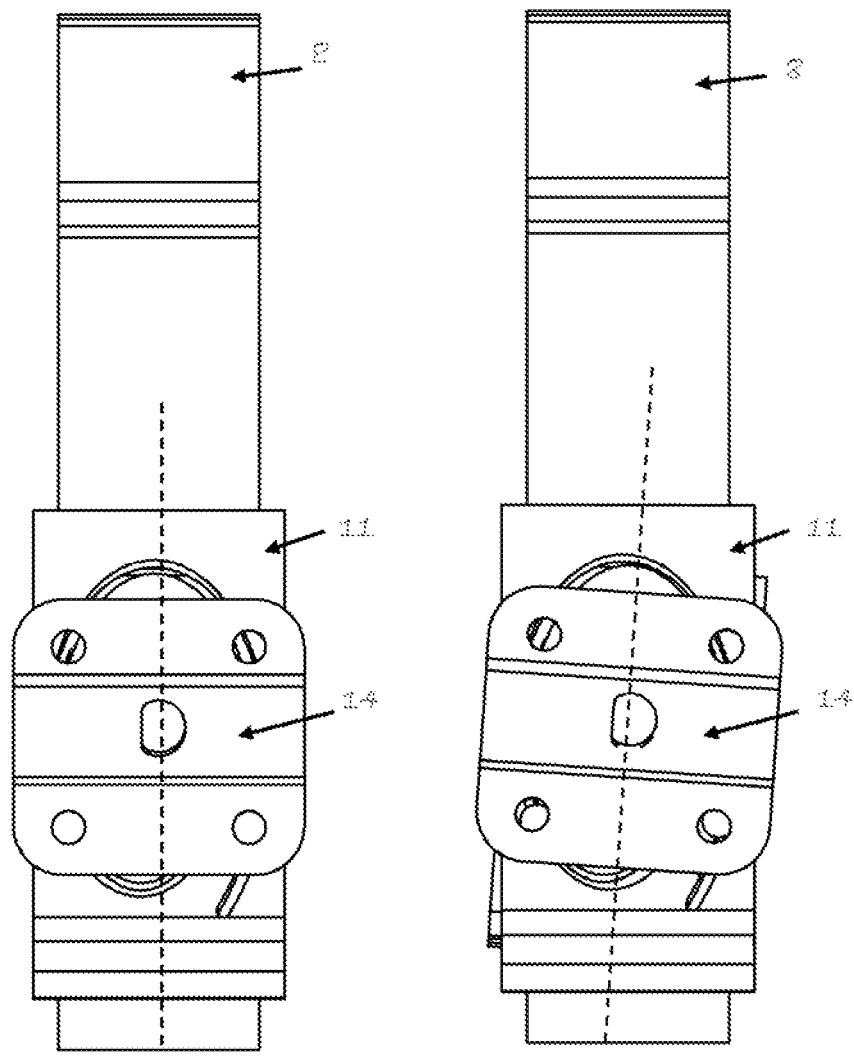
FIGS. 16c and 16d are top plan views of the embodiment shown in FIGS. 13 through 15 showing how our self-aligning adapter provides rotational alignment in the transverse plane.

While FIGS. 13, 14 and 15 show the self-alignment capability of our adapter in the sagittal plane, the 6 degrees of freedom nature of the planar compliant structures allow the adapter to show similar behavior in the two other (coronal and transverse) planes of motion. FIGS. 16*a* (level with no rotation) and 16*b* (rotated by about 5 degrees angle) show our self-aligning adapter allowing rotational alignment in the coronal plane. FIGS. 16*c* (level and neutral) and 16*d* (about 5 degrees of rotation) show our self-aligning adapter allowing rotational alignment in the transverse plane. During walking on uneven terrain or walking on turns, the coronal and transverse plane moments increase and their alignment becomes important for balance and comfort.

A unique feature of the innovation is that it can be 3D printed. This is a one-piece, no assembly manufacturing technique. It can also be machined with conventional machine shop manufacturing tools. Finally, the product can also be manufactured with carbon fiber composites, a material known for superior strength to weight ratio. Carbon fiber is a very popular material in the prosthetic foot industry.

The first embodiment of our self-aligning adapter shown in FIGS. 3 through 6 is an add-on component. This is a self-aligning adapter that can be mounted on any commercially available foot. Essentially, the adapter is a combination of two planar compliant 6 degrees of freedom springs with unique assembly that allows them to behave non-linearly compliant during heel-rocker and stiff during ankle-rocker phases of the gait. However, other different embodiments of the same core design philosophy are possible. Also, these embodiments can involve different materials (such as aluminum alloys, titanium alloys, carbon fiber composites to name a few).

Figure 17:
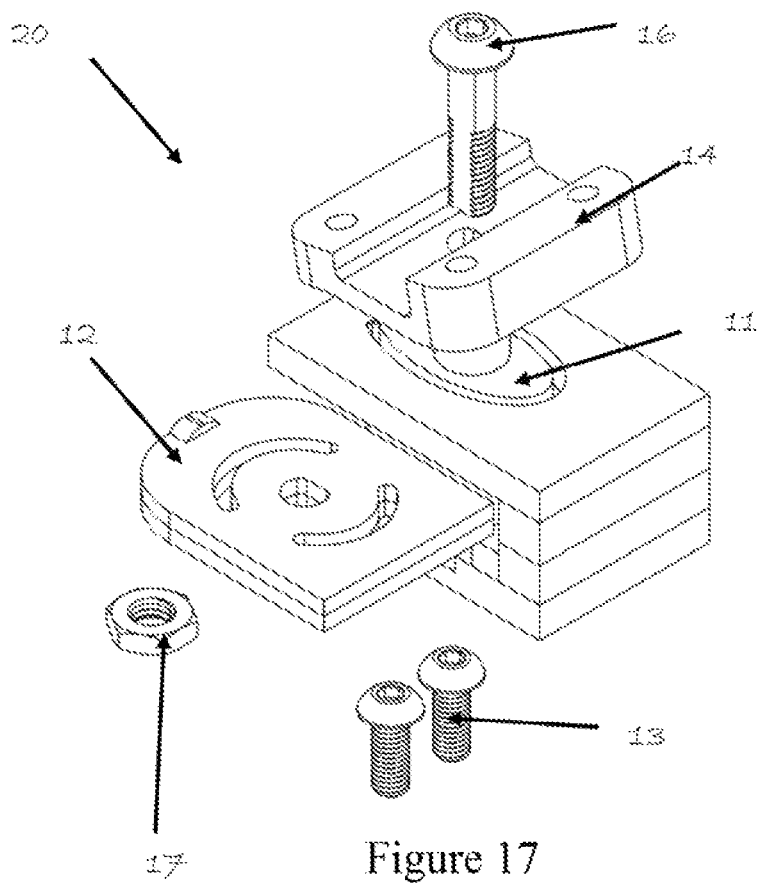
FIG. 17 is an exploded view of a second present preferred embodiment of our self-aligning adapter.
Figure 18:
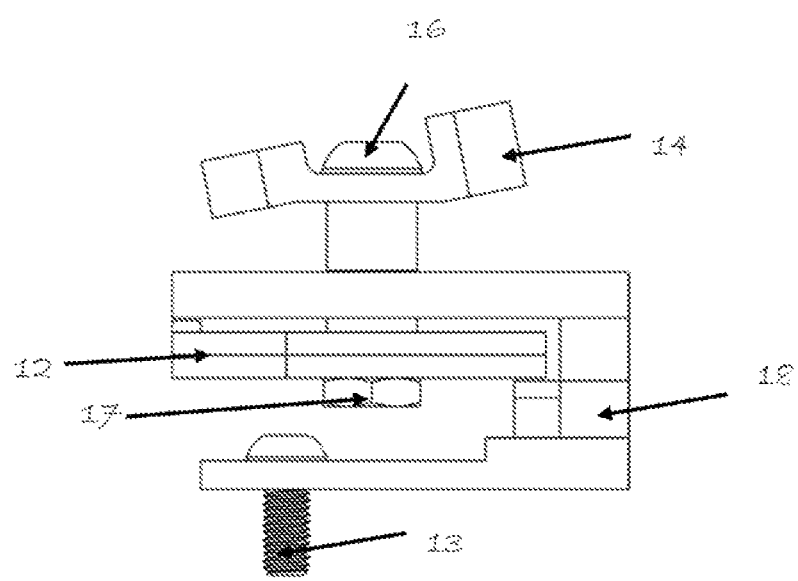
FIG. 18 is an end view of the embodiment shown in FIG. 17.

A different embodiment of our self-aligning adapter 10 is configuration 20 shown in FIGS. 17 and 18. FIG. 17 shows an exploded view, while FIG. 18 is an end view. This embodiment is made stiffer by modifying spiral geometry and employing a different material thereby rendering the use of stiffener 15 unnecessary.

The embodiments shown so far are for the product category of 'add-on component'. These are known as adapters that are mounted on prosthetic components such as socket, pylon or foot. A second product category is the ankle-foot, where the embodiment is integrated with a foot or in other words, the same design philosophy for our self-aligning adapter is integrated as an ankle to a foot structure, hence the name ankle-foot. There can be several ways to achieve this, based on the location of the claimed innovation of the 6 dof planar compliant spring (FIG. 6 or FIG. 7) in the heel (31) or keel (32) component of an ankle-foot.

Figure 19:
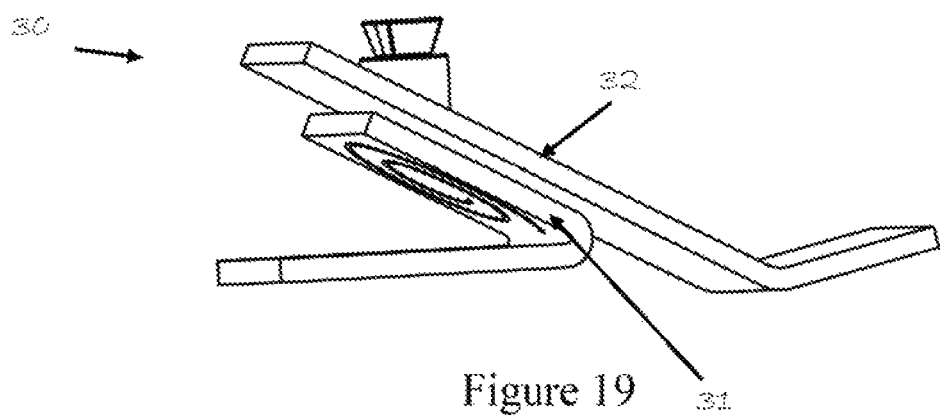
FIG. 19 is a perspective view of a third embodiment where the claimed invention of a planar compliant 6 dof spring (FIG. 7 or FIG. 8) is integrated with a foot, thereby falling in the category of ankle-foot.
Figure 20:
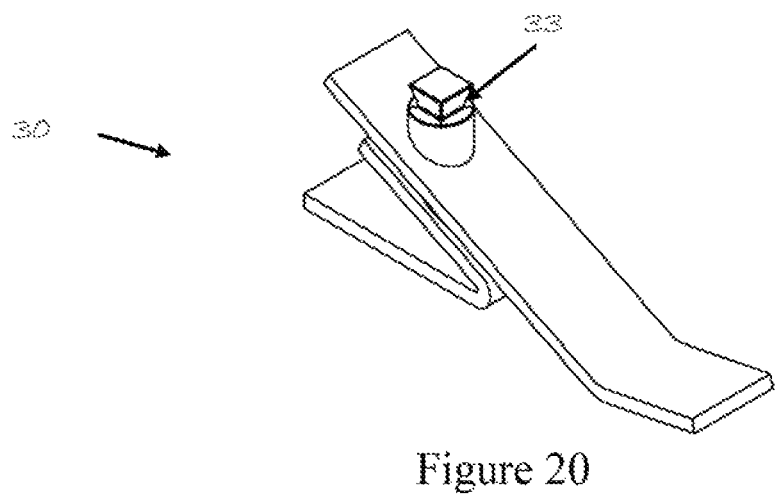
FIG. 20 is a perspective view of the ankle-foot embodiment shown in FIG. 19 from another perspective viewing angle.
Figure 21:
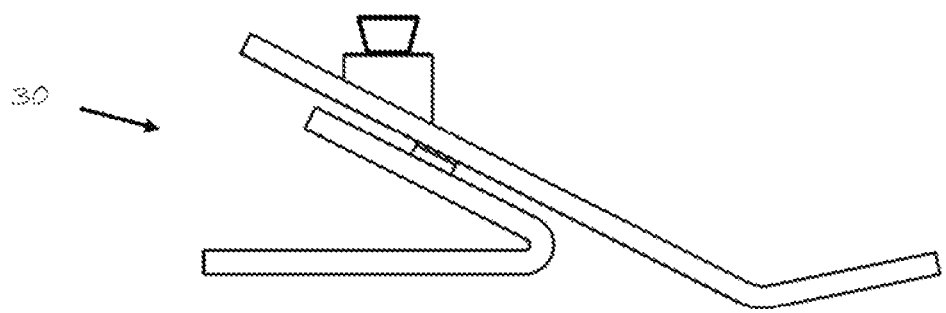
FIG. 21 is a right side view of the ankle-foot shown in FIGS. 19 and 20.

One such embodiment 30 is shown in FIGS. 19, 20 and 21. This embodiment has heel spring 31 similar to low stiffness spring 11 and a keel 32 which is functionally similar to high stiffness spring 12. This embodiment has a different connector 33 on the top to connect to the pylon 6 or socket 2.

Figure 22:
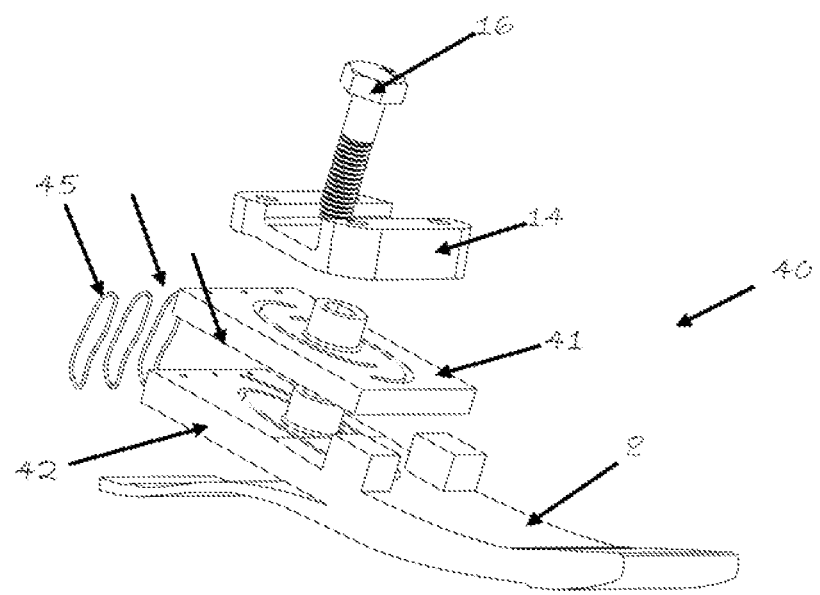
FIG. 22 is an exploded view of a fourth embodiment of our self-aligning adapter integrated to a foot.
Figure 23:
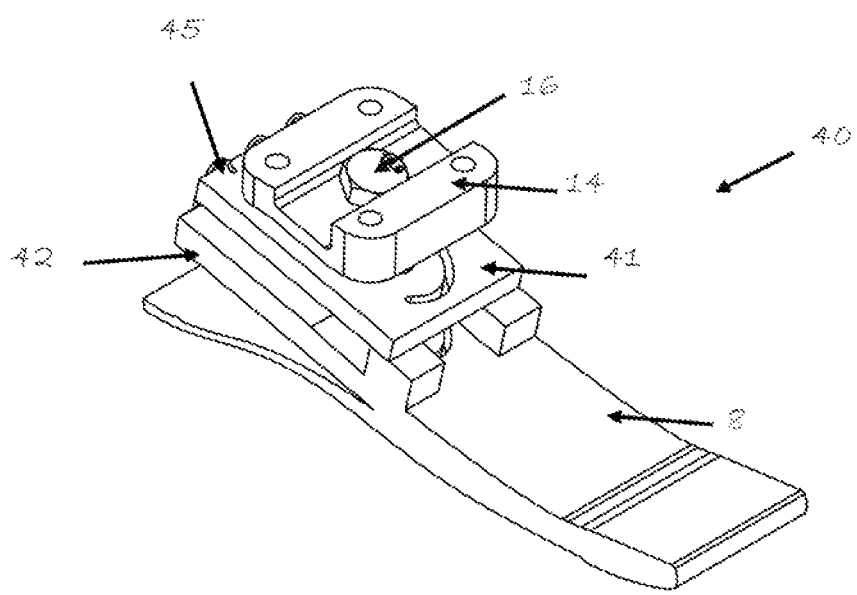
FIG. 23 is a perspective view of the embodiment shown in FIG. 22.
Figure 24:
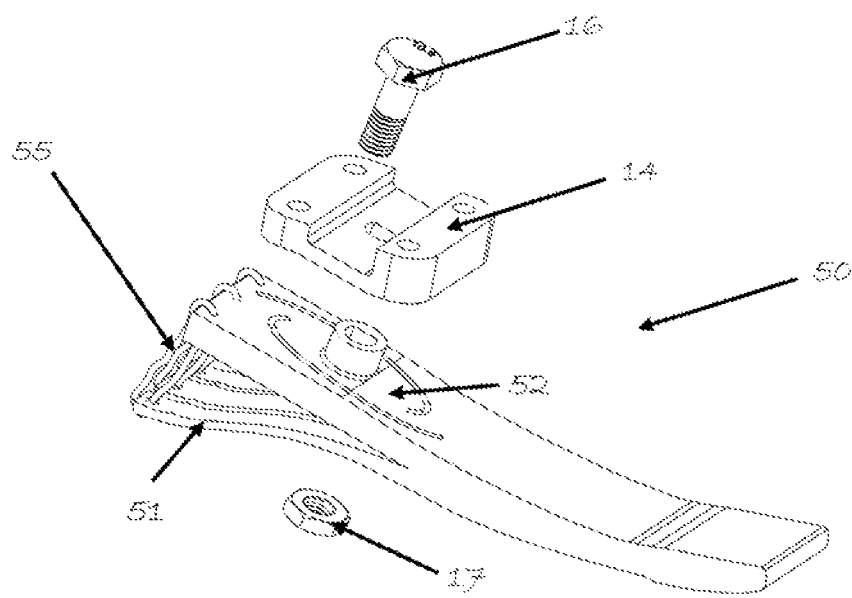
FIG. 24 is an exploded view of a fifth embodiment of our self-aligning adapter integrated to a foot.
Figure 25:
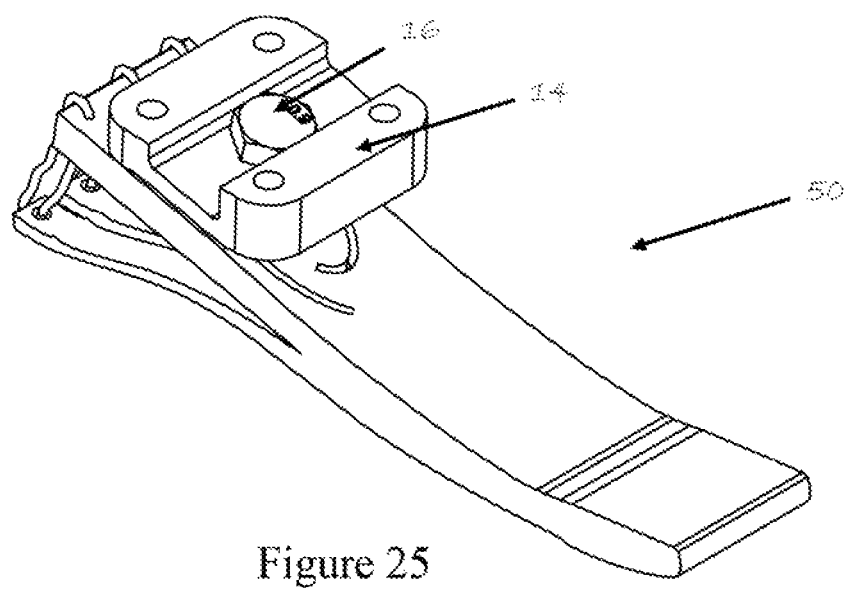
FIG. 25 is a perspective view of the embodiment shown in FIG. 24.

Another embodiment of our self-aligning adapter 10, integrated to an ankle-foot is configuration 40, shown in FIGS. 22 and 23. Another embodiment 50 is shown in FIGS.

24 and 25. These embodiments have two planar springs 41 and 42 or 51 and 52 that look different but have the same functionality. One spring 41, 51 is a low stiffness spring. The other spring 42, 52 is a high stiffness spring. The spring stiffener 45, 55 is shown in each of these embodiments as wire-like structures to reduce weight, but solid structures like spring stiffener 15 shown in FIG. 4 can also be used. All these embodiments utilize the connector 14 as well as bolt 16 and nut 17 that are in the first embodiment.

Figure 26:
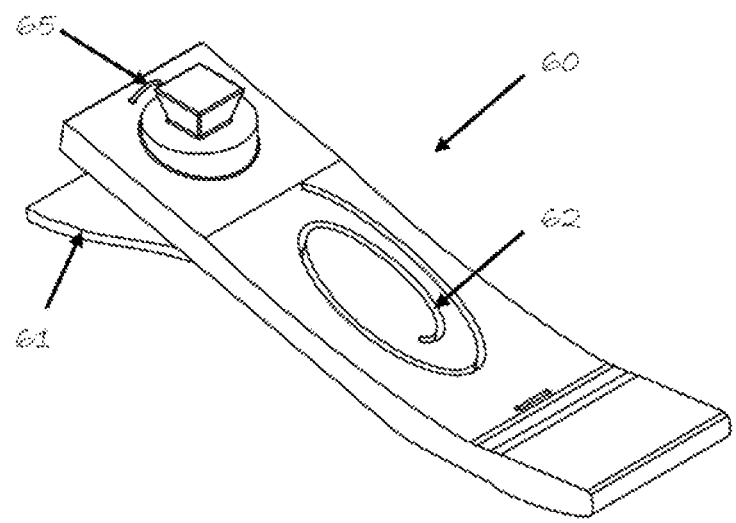
FIG. 26 is exploded perspective view of a sixth embodiment in which the heel part of the foot is modified to act like a 3 degrees of freedom spring having low stiffness.
Figure 27:
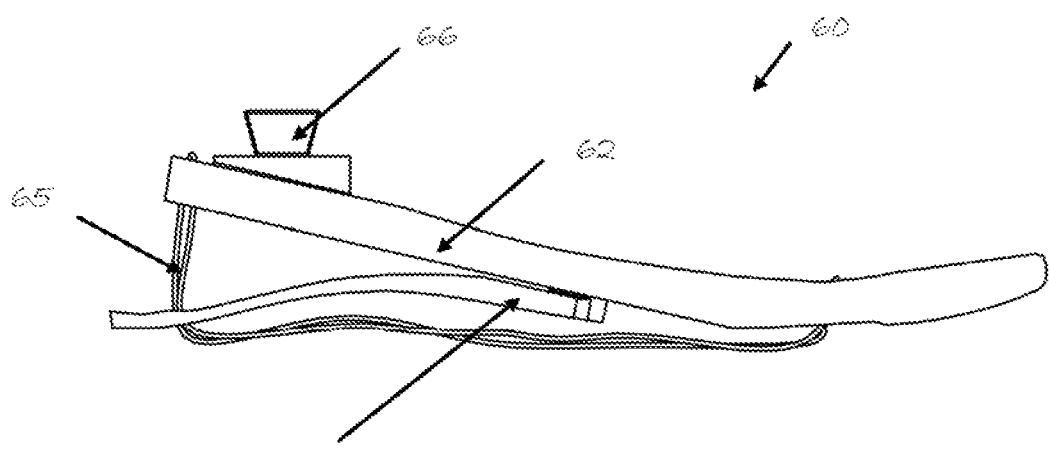
FIG. 27 is a right side view of the embodiment shown in FIG. 26.

Another possible embodiment 60 is shown in FIGS. 26 and 27 where the heel part of the foot is modified to function as the low stiffness spring 61 and another part of the foot act as the high stiffness spring 62. A non-linear stiffener 65 is connected between the two springs 61 and 62. There is a different connector 66 that is used to attach this embodiment to a pylon or leg socket. In this embodiment the foot keel (top plate) itself works as the high stiffness spring 62. The heel part of the foot is attached to it through a planar compliant structure. This low stiffness 6 degree of freedom spring allows the heel to produce the biomimetic heel-rocker region. After that, the wire-like spring stiffeners 45 become taut, and the foot keel starts to deform to produce the ankle rocker phase. This design can be a one-piece (no assembly) product, hence no exploded view is shown.

Figure 28:
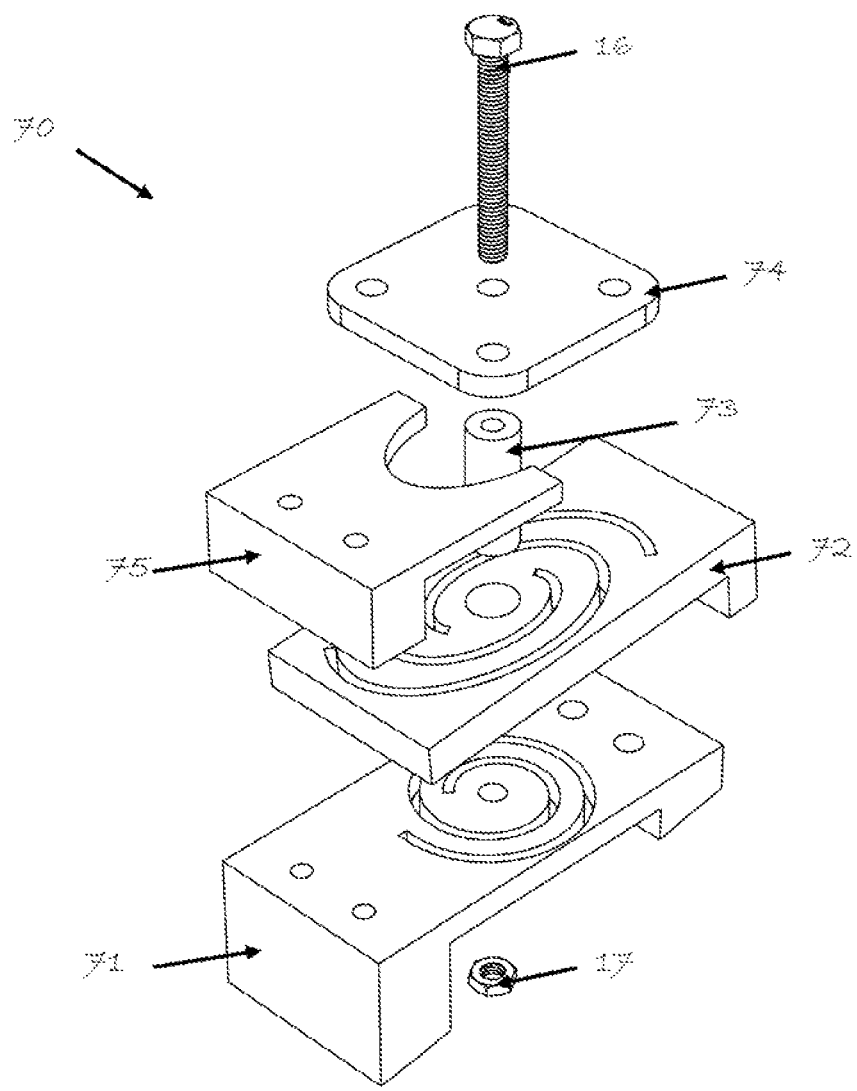
FIG. 28 is an exploded view of a seventh present preferred embodiment of our self-aligning adapter. This embodiment has the same functionality as the embodiment shown in FIG. 6.
Figure 29:
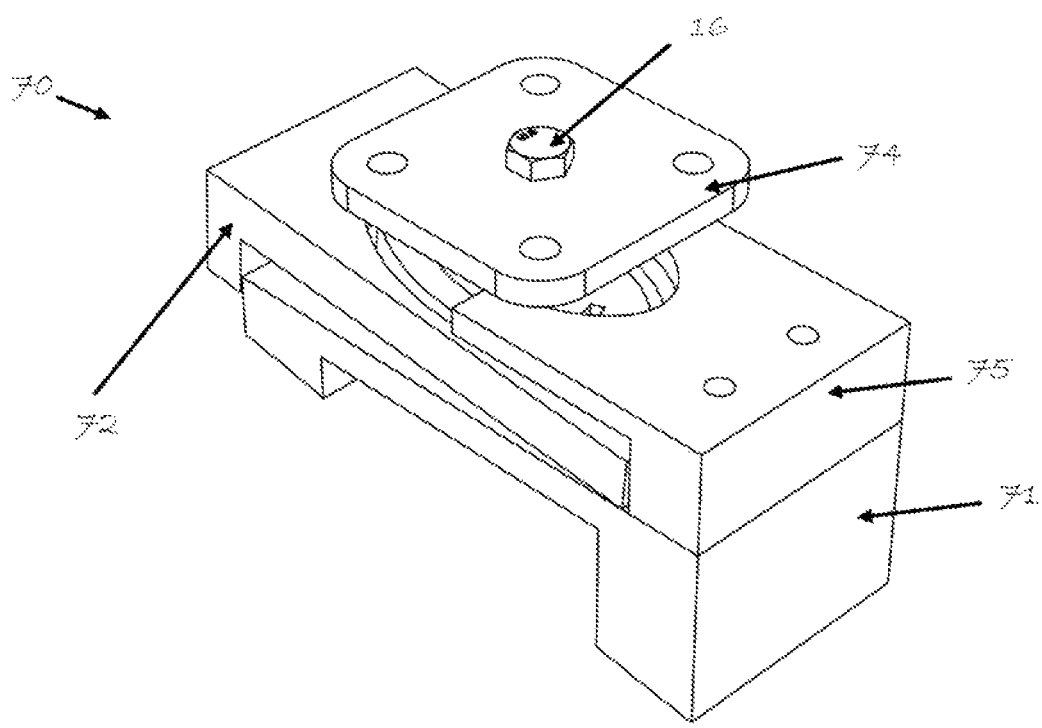
FIG. 29 is a perspective view of the embodiment shown in FIG. 28.

In another possible embodiment 70 shown in FIGS. 28 and 29 the relative position of the two 6 degrees of freedom planar compliant mechanisms are changed. In the first embodiment 10 shown in FIG. 4 the low stiffness spring 11 is located above the high stiffness spring 12. For this embodiment 70 the relative position of the low stiffness spring 71 and the high stiffness spring 72 is exactly opposite. The overall geometry of the product is changed to accommodate the non-linear stiffening mechanisms. A core rod 73 is provided through which bolt 16 passes. The core rod acts as a spacer between connector plate 74 and the high stiffness spring to accommodate the spring stiffener 75 in the assembled structure shown in FIG. 29.

Although we have described and shown certain present preferred embodiments of our self-adjusting adapter it should be distinctly understood that our invention is not limited thereto but may be variously embodied within the scope of the following claims.

We claim:

1. A self-adjusting adapter having adjustment capability in all three planes of motion through simultaneous translation and rotation for a prosthetic leg having a foot and a leg socket, the self-adjusting adapter comprising:
    a first planar spring for motion during heel-rocker, having six degrees of freedom;
    a second planar spring adjacent the first planar spring for motion during ankle rocker and six degrees of freedom;
    one of a shaft and a bolt connecting the first planar spring to the second planar spring; and
    a spring stiffener configured and positioned to increase stiffness of the second planar spring to make the second planar spring behave non-linearly.

2. The self-adjusting adapter of claim 1 wherein at least one of the first planar spring and the second planar spring has a spiral opening or curvilinear opening about a central axis of that spring.

3. The self-adjusting adapter of claim 1 wherein the first planar spring is housed within a C-shaped structure having a mouth and central cavity, the second planar spring is within the cavity and the spring stiffener covers at least a portion of the mouth.

4. The self-adjusting adapter of claim 1 wherein the first planar spring is an integral portion of a foot.

5. The self-adjusting adapter of claim 1 wherein the spring stiffener is comprised of a plurality of wires.

6. The self-adjusting adapter of claim 1 wherein the second planar spring is an integral portion of a foot.

7. The self-adjusting adapter of claim 1 wherein the second planar spring is an integral portion of a foot and the first planar spring is an integral portion of the foot.

8. The self-adjusting adapter of claim 1 wherein the second planar spring and the first planar spring have been made by 3D printing.

9. The self-adjusting adapter of claim 1 wherein the second planar spring and the first planar spring are comprised of a material selected from the group consisting of aluminum alloys, titanium alloys and carbon fiber composites.

10. The self-adjusting adapter of claim 1 wherein the first planar spring has a first stiffness and the second planar spring has a second stiffness, the second stiffness being greater than the second stiffness.

11. A self-adjusting adapter having adjustment capability in all three planes of motion through simultaneous translation and rotation for a prosthetic leg having a foot and a leg socket, the self-adjusting adapter comprising:
    a first planar spring, having six degrees of freedom, a first stiffness and a central opening;
    a second planar spring adjacent the first planar spring having six degrees of freedom, a second stiffness greater than the first stiffness and a central opening,
    one of a shaft and a bolt passing through the central opening in the first planar spring and through the central opening in the second planar spring; and
    a spring stiffener configured and positioned to increase the stiffness of the second planar spring to make the second planar spring behave non-linearly.

* * * * *